United States Patent
Zimmerle et al.

(10) Patent No.: US 11,428,639 B2
(45) Date of Patent: *Aug. 30, 2022

(54) DEVICE AND METHOD FOR DETECTION OF HUMIDITY-COMPROMISED URINE TEST STRIPS

(71) Applicant: Siemens Healthcare Diagnostics Inc., Tarrytown, NY (US)

(72) Inventors: Chris T. Zimmerle, Goshen, IN (US); Michael J. Pugia, Granger, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 196 days.

This patent is subject to a terminal disclaimer.

(21) Appl. No.: 16/894,132

(22) Filed: Jun. 5, 2020

(65) Prior Publication Data
US 2020/0300772 A1    Sep. 24, 2020

Related U.S. Application Data

(63) Continuation of application No. 15/904,823, filed on Feb. 26, 2018, now Pat. No. 10,690,597, which is a
(Continued)

(51) Int. Cl.
*G01N 21/78* (2006.01)
*G01N 33/52* (2006.01)
(Continued)

(52) U.S. Cl.
CPC ............... *G01N 21/78* (2013.01); *C12Q 1/37* (2013.01); *G01N 21/81* (2013.01); *G01N 33/493* (2013.01);
(Continued)

(58) Field of Classification Search
None
See application file for complete search history.

(56) References Cited

U.S. PATENT DOCUMENTS

| | | |
|---|---|---|
| 5,408,535 A | 4/1995 | Howard, III et al. |
| 5,477,326 A | 12/1995 | Dosmann |

(Continued)

FOREIGN PATENT DOCUMENTS

| | | |
|---|---|---|
| EP | 0837320 | 4/1998 |
| EP | 0994343 | 4/2000 |

(Continued)

OTHER PUBLICATIONS

Hilderbrand, S. A. et al. Near infrared fluorescence-based bacteriophage particles for ratiometric pH imaging, 2008, Bioconjugate Chemistry, vol. 19(8), pp. 1635-1639.
(Continued)

*Primary Examiner* — Xiaoyun R Xu

(57) ABSTRACT

The timing of the reaction of moisture-sensitive reagents for detecting the presence of analytes, e.g. leukocytes in urine samples, is used to detect when the reagents have been compromised by excess humidity. The ratio of light reflectance at wavelengths characteristic of the products of reaction between the reagents and the analyte and an infra-red reference dye is measured at two preset times after a urine sample has been applied to a test strip and used to determine whether the reagents have been compromised by excessive humidity. The presence of unusually dark samples is determined from the reflected light at 470 and 625 nm in order to confirm that the test strips are humidity-compromised.

12 Claims, 1 Drawing Sheet

Related U.S. Application Data continuation of application No. 14/838,766, filed on Aug. 28, 2015, now abandoned, which is a continuation of application No. 13/144,750, filed as application No. PCT/US2010/020998 on Jan. 14, 2010, now Pat. No. 9,145,576.

(60) Provisional application No. 61/147,272, filed on Jan. 26, 2009.

(51) Int. Cl.

| | | |
|---|---|---|
| *G01N 33/493* | (2006.01) | |
| *G01N 21/81* | (2006.01) | |
| *C12Q 1/37* | (2006.01) | |
| *G01N 21/75* | (2006.01) | |
| *G01N 21/77* | (2006.01) | |

(52) U.S. Cl.
CPC ..... *G01N 33/523* (2013.01); *G01N 2021/757* (2013.01); *G01N 2021/7773* (2013.01)

(56) References Cited

U.S. PATENT DOCUMENTS

| | | | |
|---|---|---|---|
| 5,512,450 | A | 4/1996 | Johnson et al. |
| 5,663,044 | A | 9/1997 | Noffsinger et al. |
| 5,877,863 | A | 3/1999 | Ross et al. |
| 6,239,445 | B1 | 5/2001 | Shaeef |
| 6,316,264 | B1 | 11/2001 | Corey et al. |
| 6,770,764 | B2 | 8/2004 | Corey et al. |
| 6,955,921 | B2 | 10/2005 | Corey et al. |
| 7,001,737 | B2 | 2/2006 | Rehm et al. |
| 2003/0125577 | A1 | 7/2003 | Corey et al. |
| 2004/0180444 | A1 | 9/2004 | Rannikko et al. |
| 2005/0123441 | A1 | 6/2005 | Unkrig et al. |
| 2007/0043519 | A1 | 2/2007 | Zimmerle |

FOREIGN PATENT DOCUMENTS

| | | |
|---|---|---|
| JP | 62-157554 | 7/1987 |
| JP | H08220090 | 8/1996 |
| JP | 2005156544 | 6/2005 |
| JP | 2007507716 | 3/2007 |

OTHER PUBLICATIONS

Medialab, Procedure caution from chemical screening of urine by reagent strip, 2009, retrieved from internet site: <http:/web.archive.org/web/20090112060925/http://www.medialabinc.net/spg13-0903/procedure.sub.-caution.aspx>.

International Search Report of International Application No. PCT/US2010/020998 dated Mar. 9, 2010.

Written Opinion of International Application No. PCT/US2010/020998 dated Aug. 4, 2011.

Supplementary European Search Report of European Patent Application No. EP 10733768 dated Jun. 20, 2012.

Schulman et al., "Novel Humidity Check with MULTISTIX(R) 10SG Urine Strips on the CLINITEK Status(R) Analyzer from Siemens Healthcare Diagnostics", Clinical Chemistry, vol. 55, No. 6, Supplement, 2009.

European Search Report and Search Opinion of European Patent Application No. 13005493.5 dated Apr. 17, 2014.

Smith et al., "The Use of Near-Infrared Reflectance Spectroscopy to Predict the Moisture, Nitrogen, Calcium, Total Phosphorus, Gross Energy, and Phytate Phosphorus Contents of Broiler Excreta", 2001, Poultry Science, vol. 80(3), pp. 314-319.

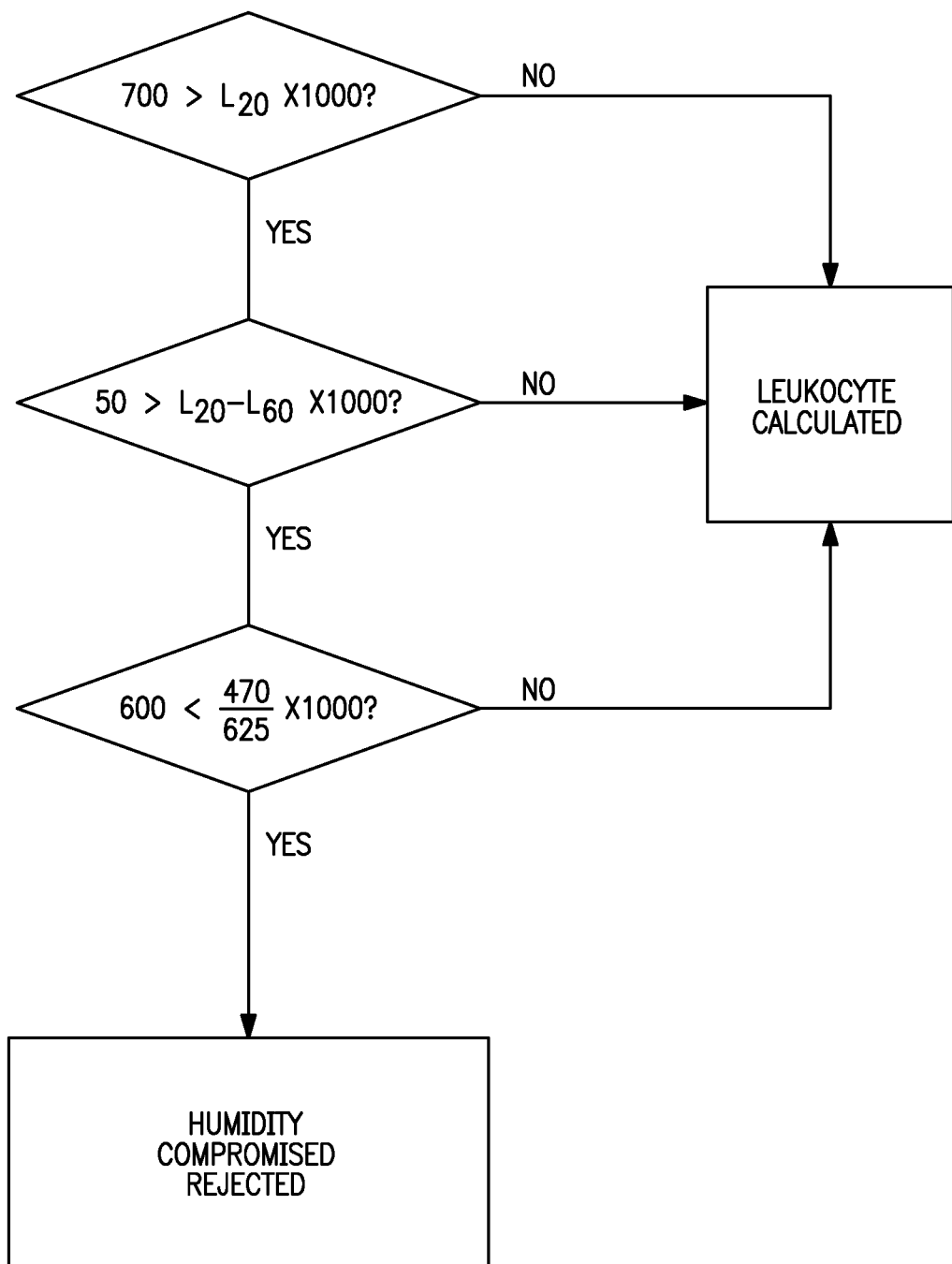

DEVICE AND METHOD FOR DETECTION OF HUMIDITY-COMPROMISED URINE TEST STRIPS

CROSS REFERENCE TO RELATED APPLICATIONS/INCORPORATION BY REFERENCE STATEMENT

The subject application is a continuation of U.S. Ser. No. 15/904,823, filed Feb. 26, 2018; which is a continuation of U.S. Ser. No. 14/838,766, filed Aug. 28, 2015, now abandoned; which is a continuation of U.S. Ser. No. 13/144,750, filed Jul. 15, 2011, now U.S. Pat. No. 9,145,576; which is a US national stage application under 35 USC § 371 of International Application No. PCT/US2010/020998, filed Jan. 14, 2010; which claims priority under 35 USC § 119(e) to U.S. Provisional Application No. 61/147,272, filed Jan. 26, 2009. The entirety of each of the above-referenced patents and patent applications are hereby expressly incorporated herein by reference.

BACKGROUND

The present disclosure relates generally to improving the performance and reliability of test strips employing moisture-sensitive reagents, particularly those used to determine the presence of analytes in urine samples, such as albumin, protein, creatinine, nitrate, uristatin, leukocyte esterase (white blood cells), occult blood (red blood cells), ketones, glucose, bilirubin, urobilogen and others familiar to those skilled in the art. Measurement of proteases and protease inhibitors such as leukocyte esterase (human elastase) or urinary trypsin inhibitor (Bikunin, Uristatin) are especially important in that they may indicate infections of the kidney or urogenital tract. These proteases and protease inhibitor strips rely on hydrolysis of proteolytic substrates by proteases to generate detectable signals. Since the biochemical reactions require water for enzymatic hydrolysis to occur, they tend to be sensitive to moisture and may interfere with the detectable signals through background reactions.

U.S. Pat. No. 5,663,044 is incorporated herein by reference. This patent describes the background art in the field of detecting leukocyte, esterase or protease and for teaching generally the use of a composition including a diazonium salt, one of a group of esters subject to hydrolysis in the presence of leukocyte, esterase or protease and an alkaline earth metal. The '044 patent teaches the measuring of reflectance of light at about 570 nm to determine the amount of leukocytes in the urine sample. The reflectance at 570 nm is compared with a standard measurement of reflectance at 690 nm. The patent indicates that the presence of alkaline earth metal promotes stability of the diazonium salt. It also suggests that the alkaline earth metal absorbs moisture which can cause background color change. Experience has shown that this reagent system is sensitive to moisture and that the test strips must be kept in a dry environment before use. The moisture content of test strips should be kept below 2 wt % to avoid degrading performance. However, measuring moisture in test strips is not very accurate. There is a particular need to measure moisture content very accurately to assure that test strips are stable in a closed dry container over several years.

Another example of the use of moisture-sensitive reagents is discussed in U.S. Pat. Nos. 6,770,764; 6,955,921; and 7,001,737 incorporated herein by reference. In the reactions described, the presence of urinary trypsin inhibitors in a urine sample is detected by adding a sample to test strips containing a known amount of trypsin, a trypsin substrate, i.e. arginine esters hydrolyzed by trypsin to produce an alcohol, and a diazonium salt. When trypsin inhibitors are present, they inhibit the reaction between trypsin and the substrate. This reduces the color produced by diazonium salt from its reaction with the phenol produced when the trypsin substrate reacts with the known amount of trypsin. By measuring the color produced, the presence of trypsin inhibitors can be determined.

In U.S. Pat. No. 6,316,264 an infra-red (IR) dye is added to a predetermined location on reagent strips in order to assure that the strips are properly aligned in the instrument used to detect and/or measure the presence of analytes in a sample applied to the strip. The IR range for the dyes was broadly between 700 and 2500 nm, but dyes having strong absorbance in the range of 825-855 nm were said to be desired in certain non-limiting embodiments, with absorbance in the visible range (400-700 nm) less than 20%.

As suggested above, it would be advantageous if urine test strips that are moisture-compromised could be identified with improved accuracy to prevent unsafe use and to correct for moisture-affected results. Since reagents which involve hydrolysis of proteolytic substrates are especially sensitive to moisture, if the reagents themselves could be used to indicate the presence of undesirable moisture, significant improvement would have been obtained. The present disclosure provides such a method, which will be described in detail below.

BRIEF DESCRIPTION OF THE DRAWINGS

The sole FIGURE is a flow chart for either determining leukocyte content of a sample or rejecting the result as humidity-compromised.

DETAILED DESCRIPTION

The present disclosure has application to moisture-sensitive test strips that are used to measure hydrolysis of proteolytic substrates used to detect protease or protease inhibitors. One example is found in the detection of leukocyte, esterase or protease, as described in U.S. Pat. No. 5,663,044. Another example is found in the detection of urinary trypsin inhibitors described in U.S. Pat. Nos. 6,770, 764; 6,955,921; and 7,001,737.

In general, the present disclosure is a method of detecting excessive moisture in test strips employing moisture-sensitive reagents. By measuring color or other response developed by moisture-sensitive reagents just after applying a sample and comparing the result to a known infra-red reference dye, moisture-compromised reagents are identified and the result can then be flagged or discarded.

When the developed color is measured by light reflectance, the value of the reflectance ratio (i.e. the ratio of the reflectance of the reagents to the reflectance of the reference dye) immediately after applying a sample is compared with the value of the reflectance ratio taken a short time later and used to determine the effect of excessive humidity and to reject the reagents if they are humidity-compromised. A second reflectance ratio may be measured to determine if the sample is unusually colored and may be affecting the results.

In one particular (but non-limiting) embodiment, for detecting humidity-compromised leukocyte reagents, the reagents include a diazonium salt, e.g. DNSA (1-diazo-2-naphthol-4-sulfonic acid), that reacts with a hydrolysable ester, e.g. PPTA (2-hydroxy-5-phenyl-pyrrole-N-tosyl-L-alanine ester). When leukocyte esterase is present in the urine sample, a color is produced in proportion to the amount of leukocytes present. In this embodiment, the reflectance at light wavelength of 520-570 nm is compared with the reflectance of about 825 nm characteristic of the reference dye.

The present disclosure includes an improved method of measuring hydrolysis of proteolytic substrates in urine samples applied to test strips. In general, reagents based on proteolytic substrates can be used to detect any protease. The amino acid sequence of the reagents is matched to the type preferred by the protease being detected and the amino acid sequence is attached to a signal generating moiety that upon hydrolysis forms the signal. An example of this principle is detection of leukocyte esterase, which is used to detect the presence of leukocytes in a sample, as described in U.S. Pat. No. 5,663,044. The presence of leukocytes is correlated with the reflectance of light at the characteristic wavelength of the reagents with reference to the reflectance of light at a characteristic wavelength of an infra-red reference dye. The measured reflectance comparison is correlated with the presence of leukocytes after an incubation time of about 20 seconds to 3 minutes after application of a urine sample to the reagents. Such test strips may be compromised by excess humidity, which can reduce reagent activity and falsely show color development indicative of the presence of leukocytes in a urine sample. By measuring the ratio of reflectance from the reagents to the infra-red reference dye during the first minute after a urine sample has been applied to reagents, the method of the present disclosure determines whether the reagents have been compromised by excess humidity.

Reagents based on proteolytic substrates can also be used to detect a protease inhibitor. Again, the amino acid sequence is matched to the type preferred by the protease inhibitor, the sequence being attached to a signal generating moiety that upon hydrolysis forms the signal. The protease is added to the reagent and therefore generates a signal when inhibitor is not present in the sample. The absence of a signal is used to determine the presence of protease inhibitor in a sample. An example of this principle is detection of urinary trypsin inhibitor as described in U.S. Pat. Nos. 6,770,764; 6,955,921; and 7,001,737.

Hydrolysis of a proteolytic substrate does not reach the reaction endpoint in the short time frame of less than a few minutes needed for strips used in point-of-care applications. The hydrolysis reactions continue to create a signal with time and are typically measured kinetically to allow readings that are not dependent on timing by the operator. For example, the color developed by the reaction for leukocytes in urine can be measured at 20 and 60 seconds and the ratio the of signals at both times used as a kinetic result, that is, showing the rate of color change. This avoids the user having to wait for a full 3 minutes to obtain a result.

The present disclosure is applicable to many formats in which the reagents are moisture-sensitive. That is, the reagents can react in the presence of moisture and falsely indicate the presence of an analyte, which is not actually present in the sample being measured. Examples of such moisture-sensitive reagents have been mentioned above. Of particular importance to the present inventors was the sensitivity of moisture of reagents used to detect leukocytes in urine samples by esterase in the leukocytes, as discussed below with reference to one particular (but non-limiting) embodiment. However, it will be evident that the methods of the present disclosure have application to other moisture-sensitive reagents, including, but not limited to, other reagents that can be used to measure the presence of leukocytes. It is understood that test strips can have many formats, including, but not limited to, dipsticks and lateral flow cartridges.

Leukocyte Reagent Chemistry

Leukocyte reagents useful in the present disclosure that can provide a method of measuring the leukocyte content of urine samples are discussed in U.S. Pat. No. 5,663,044 mentioned above. A particular (but non-limiting) embodiment of the composition of the present disclosure was described in Table 4 of the '044 patent. An alanine compound (PPTA; 2-hydroxy-5-phenyl-pyrrole-N-tosyl-L-alanine ester) served as a substrate for leukocyte esterase, which hydrolyzes PPTA, after which the hydrolyzed product reacts with the diazonum indicator (DNSA; 1-diazo-2-naphthol-4-sulfonic acid) to produce color. The color was measured by the degree of reflectance when examined at a light wave length of 520-570 nm (570 nm in the '044 patent). The reflectance at 520-570 nm was related to a standard wavelength at 690 nm. This comparison was used to compensate for differences in the white background color of the strip substrate, which was white cellulose on a white polystyrene having a reflectance>60%, and approaching colorless at wavelengths>~690 nm. The white background color is particularly sensitive to moisture and a small amount can cause a large change in reflectance ratio. The white background is also sensitive to the color of urine and small amounts can cause large changes in reflectance ratio. As a result, such a reflectance ratio cannot be used to accurately measure moisture after dipping the strip in urine.

In the present disclosure, an infra-red reference dye is added having a characteristic response to light at a wavelength at least 120 nm greater than the 520-570 nm range. It has been found that the wavelength of the IR dye and the amount used affect the accuracy of measurements by reducing background interference. The addition of an IR dye to the leukocyte reagents provides a lower background color of <=60% reflectance at >=700 and 2500 nm. This lower background reduces the effect of urine color on the reflectance ratio, but not the effect of moisture. Thus, the reflectance ratio can be used to accurately measure moisture after dipping a sample in urine.

However, this lower background color of <=60% reflectance at >=700 and 2500 nm can reduce ability of the reagents to detect the hydrolysis of proteolytic substrates. This effect is shown in the following table, where the effect of the reagent substrate background color is reduced as the amount of the IR dye is increased. The amount of IR dye that a reagent can tolerate depends on the reference wavelength used to measure the background, the signal wavelength of the substrates, the sensitivity of the substrate for moisture, and the sensitivity of the substrate for protease hydrolysis and the amount of background dye signal<700 nm. The tolerance of any given hydrolysis substrate can be determined as shown in Table 1 where the desired reduction of background interference relative to color in the sample occurs at greater than 0.2 mg/dL, or about 0.5 wt % relative to the reference dye. However, when the dye quantity is raised as high as 20 mg/dL the reflectance ratio is increased to 1.6 and the signal is reduced from the ~1.0 signal expected. Thus, the amount of dye used should be limited to that needed to minimize background interference.

TABLE 1

| Dye (1) mg/dL | Reflectance Ratio 570/690 nm (2) | Background Interference (3) |
|---|---|---|
| 20 | 1.649 | 3% |
| 2 | 1.042 | 4% |
| 0.2 | 0.976 | 5% |
| 0.02 | 0.967 | 22% |
| 0 | 0.964 | 45% |

(1) DTO 141 which is Dye 3 in Table 2 of U.S. Pat. No. 6,316,264 and has the chemical name 3-(5-carboxypentyl)-2-[2-[3-[[3-(5-carboxypentyl)-1, 3-dihydro-1, 1-dimenthyl-2H-benz[e]indol-2-ylidene] ethylidene]-2-(n-hexylthio)-1-cyclohexen-1-yl] ethenyl]-1, 1-dimethyl-1H-benz[e] indolium, inner salt.
(2) Reaction to 42 cell/uL leukocytes in urine in medium specific gravity urine and measured using the CLINITEK Status ® instrument (Siemens Healthcare Diagnostics).
(3) Difference between highly colored brown clinical urine and a typically colored yellow urine. Both urines lacked leukocytes and were measured using the CLINITEK Status ® instrument.

In the above experiment the leukocyte reagent was made from two sequential saturations of filter paper. The first saturation was with an aqueous mix containing boric acid, Bio-Terge AS40, PVP polymer and NaCl to control ionic strength. The mix pH was adjusted to 8.8 to 9.3 using sodium hydroxide or hydrochloric acid. The second saturation was an acetone/DMSO solvent mix containing DNSA, PPTA, decanol and boric acid. Each ingredient's functions, particular (but non-limiting) concentration, and allowable range are given in Table below. The mix solutions were used to saturate filter paper, in this case 205C grade Ahlstrom filter paper, and the paper dried at 121° C. for 9 minutes after the first saturation, and at 100° C. for 7 minutes after the second saturation. The resultant dry reagent was processed into reagent strips which were tested using the CLINITEK Status® instrument.

TABLE 2

| Ingredient | Function | Particular Conc. used | Allowable Range |
|---|---|---|---|
| $1^{st}$ Application | | | |
| Water | Solvent | 1000 mL | — |
| NaCl | Ion Strength Agent | 14.6 g | 1-30 g/L |
| Bio-Terge AS40 | Surfactant | 2 g | 0-4 g/L |
| Boric acid | Buffer | 24.7 g | 5-35 g/L |
| PVP | Polymer | 20.0 g | 5-50 g/L |
| $2^{nd}$ Application | | | |
| Acetone | Solvent | 955 mL | — |
| DMSO | Solvent | 30 mL | 10-60 mL |
| DNSA | Diazonium indicator | 0.174 g | 0.050-0.5 g/L |
| PPTA | Enzyme substrate | 0.422 g | 0.10-0.8 g/L |
| Decanol | Enzyme activator | 15 mL | 5-40 ml/L |
| Boric Acid | Buffer | 0.5 g | 0-3.0 g/L |

DNSA = 1-diazo-2-naphthol-4-sulfonic acid
PPTA = 2-hydroxy-5-phenyl-pyrrole-N-tosyl-L-alanine ester Various dyes could be used, including those described in U.S. Pat. No. 6,316,264 incorporated herein by reference and having characteristic absorbance in the infrared region of about 700 to about 2500 nm. Examples include phthalocyanine and naphthalocyanine compounds, metal complex dyes (e.g. dithiolene metal complex dyes) and polymethine dyes, including cyanine dyes. Other dyes include di and triphenylmethane dyes, quinone dyes, azo dyes, and charge transfer and charge resonance dyes. Their common characteristic being that reflectance of light at a unique wavelength is measured at least 120 nm above that of the reagent wavelength. In connection with the leukocyte reagents discussed above, the dye should have a characteristic reflectance of at least 700 nm, such as (but not limited to) above 700 and less than 2500 nm.

Although including the reference dye with the leukocyte reagents is a particular (but non-limiting) embodiment, it also is possible to place the reference dye at another location, as was done for purposes of aligning a test strip (U.S. Pat. No. 6,316,264). The changes due to moisture that occur when the dye contacts the sample may differ from those that occur when the dye is within the reagents. However, such differences can be accommodated by those familiar with the art.

Detecting Moisture Contamination in a Leukocyte Test Strip

As discussed above, moisture causes the leukocyte reagents to degrade and produce a false color change. The enzymes in leukocytes are not needed to hydrolyze the proteolytic substrate, e.g. PPTA. It has been found that the reagents are sensitive to as little as 0.1% moisture on a leukocyte reagent pad. The rate of color change is essentially directly proportional to the amount of water present. The importance of humidity control is evident when after 10 minutes exposure to >60 Relative Humidity the test provides false positive results.

This sensitivity to moisture is used in the present disclosure to determine whether a reagent pad has been contaminated with moisture. The color change is determined first at about 20 seconds after a urine sample has been applied. If color is detected after 20 seconds, then moisture contamination is suspected. This is confirmed if the color has not significantly increased after 60 seconds, that is, the activity of the reagents has been reduced. This method was confirmed in an experiment in which test strips were exposed to 30° C. at 80% humidity for 10 minutes, conditions known to cause failure of the reagents. Twenty three of twenty four strips were found to have failed when the ratio of the reflectance at 520 nm to the reflectance at 820 nm was used. The amount of the DTO 141 dye applied was 0.2 mg/dL, relative to 42 mg/dL of PPTA of the leukocyte reagents. A parallel experiment in which only the reflectance at 520 nm was measured, i.e. without dye present, failed to detect moisture contaminated strips in 42% of the strips, this was also true when a reflectance ratio of 520 nm/870 nm was used, but without dye present.

The influence of color in the urine sample also is accounted for in the method of the present disclosure. The sample color is measured by the absorbance of light at about 460 nm (within the visible range). In order to affect the measurement of color developed by the leukocyte reagents a new ratio is determined, i.e. reflectance at about 460 nm (for sample color) divided by reflectance at about 625 nm. This ratio prevents dark urine samples from being considered to be humidity-compromised. If the ratio (times 1000) is above 600 the sample color is light and reflectance is high. If so, then the strip being tested will be confirmed as humidity-compromised if the reflectance ratios at 20 and 60 seconds have indicated that the strip is responding in an abnormal manner. If the ratio is below 600, the sample has a dark color which may have affected the results and the strip is not rejected if the results at 20 and 60 seconds have been satisfactory.

The difference between the ratio of reflectance at 525 nm to reflectance at 825 nm taken at 20 and 60 seconds after applying a sample is used to determine whether the reagents have been degraded by moisture. In general, if the first reading (20 sec) gives a ratio of less than about 700 (ratio×1000), then excess humidity is indicated since reflectance at 525 indicates significant color had been already developed. If the second reading is taken at 60 seconds and compared with the first reading and the difference in the readings is less than about 50 (ratio×1000), then the presence of excess humidity is confirmed since the reagents have lost their normal activity.

For example, three values are measured when the reagents include PPTA and DNSA and the reference dye is DTO 141.

TABLE 3

|  | Ratio, nm | Time | Critical value ratio × 1000 | meaning |
|---|---|---|---|---|
| $L_{20}$ | 525/845 | 20 sec. | <700 | High absorption Excess humidity likely |
| $L_{60}$ | 525/845 | 60 sec | $L_{20}$-$L_{60}$ < 50 | Humidity reducing reagent activity |
| H | 470/625 | 40 and 60 seconds | >600 | High reflectance Sample light colored |

Applying those values to the readings according to the procedure shown in FIG. 1 provides for rejection of results as humidity-compromised or for reporting leukocyte measured in the sample. In an example, a CLINITEK Status® instrument is used to analyze the urine sample for the presence of leukocytes. An absorbent strip (e.g. filter paper) saturated with reagent solutions as described above in Table 2 has a urine sample applied to it and the resulting color changes are measured by light reflectance in the CLINITEK Status® instrument according to the inventive procedure.

If the measured value of $L_{20}$-$L_{60}$ is less than 50, it is possible that excessive humidity has reduced leukocyte reagent activity. If above 50, then the value of $L_{20}$-$L_{60}$ can be used in calculating leukocyte concentration in the sample. However even if below 50, the 525/845 nm ratio may still be able to provide a leukocyte concentration. The initial value of the 525/845 nm ratio ($L_{20}$) is considered. If the value is below 700 (ratio×1000) then high absorption of light at 525 nm is indicated, suggesting that excess humidity may have been present in the test pad. Combined with the result of $L_{20}$-$L_{60}$ then, it is likely that the leukocyte reagents have been compromised by excess humidity. But, since the results may have been influenced by an unusually dark sample, the ratio H, 470/625 nm, is measured. If the result is above 600 (ratio×1000) high reflectance is indicated, meaning that the sample is not highly colored. If so, then the leukocyte reagents are considered to have been compromised by high humidity. If the sample is dark, i.e. the critical ratio H is below 600, but the previously determined values of $L_{20}$-$L_{60}$ and $L_{20}$ were acceptable, then the sample is considered not to be compromised and the leukocyte content is calculated.

It should be understood that the specific light wavelengths and measurement times just described are useful for determining the presence of leukocytes in urine samples with the amounts of the reagents described. The method, however, has application more generally to many other reagents that are moisture-sensitive and yet are used to detect samples that contain water. Appropriate detection protocols should be readily established by those that are skilled in the art after having reviewed the present disclosure.

As illustrated above, the Clinitek Status® instrument is useful in carrying out the method of the present disclosure. Aspects of that instrument are described in U.S. Pat. Nos. 6,239,445; 5,877,863; 5,477,326; and 5,408,535, which are incorporated herein by reference. The Clinitek Status® instrument is a reflectance spectroscope in which a test strip carrying a sample is illuminated by a light source and light reflected from the test strip is detected and used to determine the presence and amount of the analyte in the sample. The operation of spectrophotometers is also discussed in U.S. Pat. No. 6,316,264, referred to above. As noted therein, a camera-type instrument, which creates a multipixel image may also be used to carry out the method of the present disclosure.

What is claimed is:

1. A method of analyzing a moisture-sensitive reagent disposed on a substrate and contacted with a urine sample, the method comprising:
    (a) measuring the reflectance of light at a first wavelength and a second wavelength at a first predetermined time after contacting said reagent with said sample;
    (b) measuring the reflectance of light at the first wavelength and the second wavelength at a second predetermined time after contacting said reagent with said sample, the second predetermined time being after the first predetermined time;
    (c) calculating a first ratio of the reflectance measurements in (a) and a second ratio of the reflectance measurements in (b);
    (d) determining a level of activity of the reagent between the first and the second predetermined times by comparing the first ratio and the second ratio calculated in (c);
    (e) determining a concentration of an analyte in the sample when the level of activity of the reagent determined in (d) is at or above an expected level;
    (f) when the level of activity of the reagent determined in (d) is less than the expected level, determining whether a primary cause of the less than expected activity is due to a color of the sample;
    (g) when it is determined in (f) that the primary cause is the color of the sample, determining the concentration of an analyte in the sample; and
    (h) when it is determined in (f) that the primary cause is not due to the color of the sample, identifying the primary cause as being a humidity reduced sensitively of the moisture-sensitive reagent and rejecting the moisture-sensitive reagent as being humidity compromised.

2. The method of claim 1, wherein said moisture-sensitive reagent is based on esterases hydrolyzing derivatized esters.

3. The method of claim 1, wherein said moisture-sensitive reagent is based on proteolytic substrates used to detect protease inhibitors.

4. The method of claim 1, wherein said analyte is leukocytes.

5. The method of claim 1, wherein said analyte is urinary trypsin inhibitors.

6. The method of claim 1, wherein said moisture-sensitive reagent includes a diazonium salt and an ester subject to hydrolysis in a presence of leukocytes.

7. The method of claim 1, wherein the second wavelength is separated from the first wavelength by at least about 120 nm.

8. The method of claim 1, wherein each of (a) through (h) are performed by an optical inspection apparatus.

9. The method of claim 1, wherein the first wavelength is between about 520-570 nm.

10. The method of claim 1, wherein the second wavelength is about 825 nm.

11. The method of claim 1, wherein the first wavelength or the second wavelength corresponds to a characteristic reflectance of a reference dye disposed on the substrate.

12. The method of claim 1, wherein the first wavelength or the second wavelength corresponds to a characteristic reflectance of a reference dye disposed on the substrate.

\* \* \* \* \*